(12) United States Patent
Jiang et al.

(10) Patent No.: US 7,909,995 B2
(45) Date of Patent: Mar. 22, 2011

(54) COMBINED NUTRIENT RECOVERY AND BIOGAS SCRUBBING SYSTEM INTEGRATED IN SERIES WITH ANIMAL MANURE ANAEROBIC DIGESTER

(75) Inventors: Anping Jiang, Pullman, WA (US); Tianxi Zhang, Pullman, WA (US); Craig Frear, Pullman, WA (US); Shulin Chen, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 224 days.

(21) Appl. No.: 12/132,016

(22) Filed: Jun. 3, 2008

(65) Prior Publication Data
US 2009/0206028 A1    Aug. 20, 2009

Related U.S. Application Data

(60) Provisional application No. 61/029,961, filed on Feb. 20, 2008.

(51) Int. Cl.
  *C02F 3/28* (2006.01)
  *C02F 11/04* (2006.01)
(52) U.S. Cl. .................. 210/206; 210/259; 210/903
(58) Field of Classification Search ............... 210/198.1, 210/205, 206, 259, 903, 906
See application file for complete search history.

(56) References Cited

U.S. PATENT DOCUMENTS

| | | | | |
|---|---|---|---|---|
| 4,959,088 | A * | 9/1990 | Fuderer ........................ | 62/101 |
| 5,593,590 | A * | 1/1997 | Steyskal ...................... | 210/603 |
| 6,569,332 | B2 * | 5/2003 | Ainsworth et al. ........... | 210/603 |
| 2004/0025715 | A1 * | 2/2004 | Bonde et al. ................. | 99/485 |
| 2006/0124541 | A1 * | 6/2006 | Logan et al. ................. | 210/605 |

FOREIGN PATENT DOCUMENTS

JP        57-012896 A    *   1/1982

* cited by examiner

*Primary Examiner* — Fred Prince
(74) *Attorney, Agent, or Firm* — Whitham Curtis Christofferson & Cook, PC

(57) ABSTRACT

An economical, integrated system works in series with anaerobic digestion of animal waste to recover nitrogen and phosphorous, while also scrubbing the produced biogas.

3 Claims, 8 Drawing Sheets

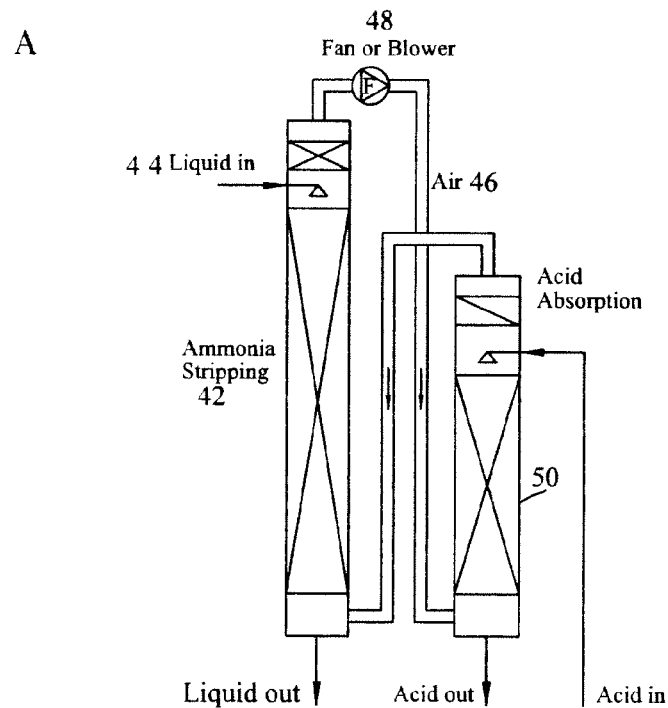
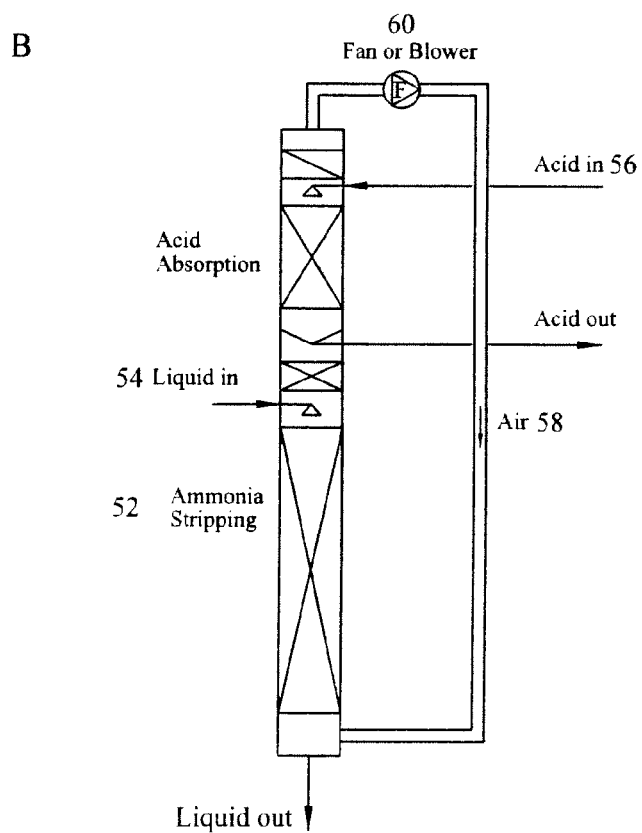
Figure 2 A-B

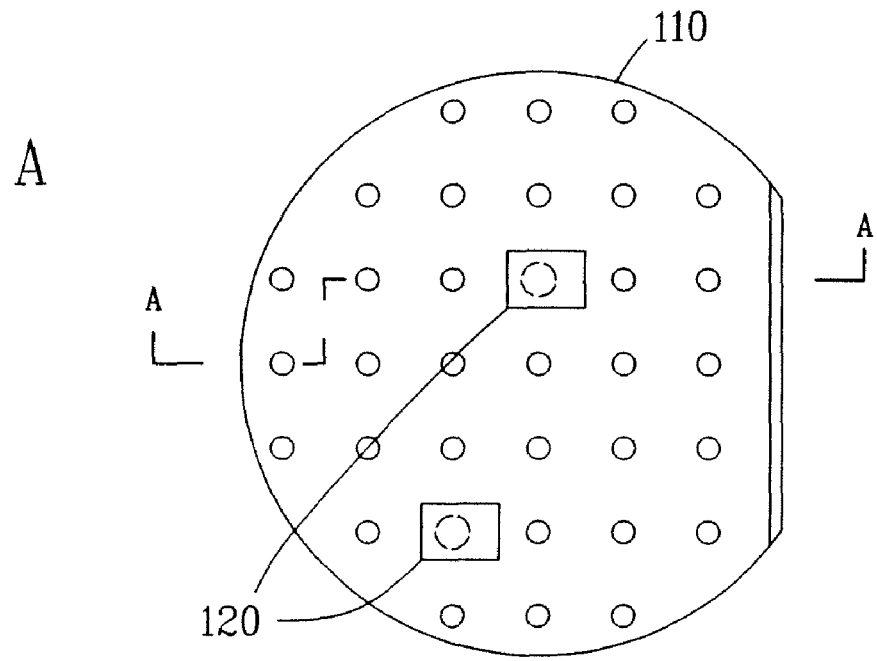
Plan View of the Tray
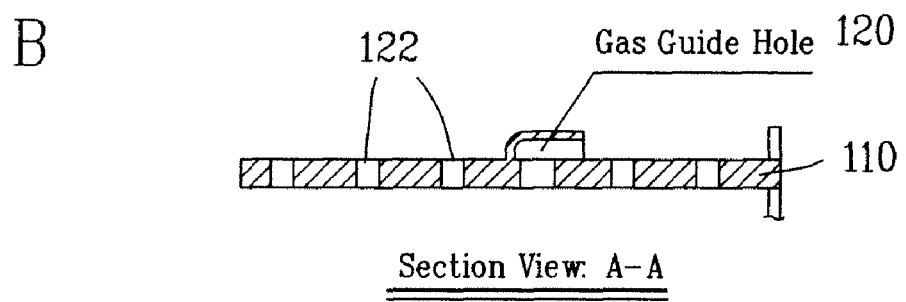
Section View: A-A
Figure 3 A and B

Tray Tower Section View

COMBINED NUTRIENT RECOVERY AND BIOGAS SCRUBBING SYSTEM INTEGRATED IN SERIES WITH ANIMAL MANURE ANAEROBIC DIGESTER

CROSS-REFERENCE TO RELATED APPLICATIONS

This application claims benefit of U.S. provisional patent application 61/029,961, filed Feb. 20, 2008, the complete contents of which are hereby incorporated by reference.

BACKGROUND OF THE INVENTION

1. Field of the Invention

The invention generally relates to the recovery of nutrients during the treatment of animal waste. In particular, the invention provides an economical, integrated system for both nutrient recovery and biogas scrubbing from the effluent and gas that results from digestion of animal waste.

2. Background of the Invention

The management of animal waste is a problem of ever increasing magnitude. It has been estimated that approximately 250 million tons of dry animal manure are produced yearly in the United States, with large amounts being generated by concentrated animal feeding operations (CAFOs). Historically, animal waste was successfully used as fertilizer on agricultural crop land. However, CAFOs generate more waste than can be disposed of in this manner without causing detrimental nutrient buildup. For example, phosphorus in runoff from such agricultural operations has been identified as a major contributor to water pollution. The use of "lagoons" to contain animal waste is now a common practice. However, there are problems associated with this method as well. Lagoons are a major source of methane gas and odors, and their capacity is also finite. Exporting of animal waste away from the agricultural operation merely shifts the location of the problem without providing a solution and transportation of the liquid waste is not economical.

A recent trend in animal manure management is the renewed interest in using anaerobic digestion (AD) technology for energy production, odor control, and waste water mitigation. As of 2007, more than 100 CAFO digesters had been built in the United States, with the vast majority having been built in just the last 5 years (EPA AgStar, 2007). Many producers have shown a commitment to AD technology because of its strengths in odor abatement, energy production and development of useful co-products such as improved fiber bedding. Although AD is advantageous in regard to methane entrapment, reduction of volatile organics, solids reduction, chemical oxygen demand, vector reduction and pathogen removal, it does not reduce or recover nutrients. This is particularly true for phosphorous, which is found both in the settled solids and the mixed-liquor effluent, and nitrogen, which is found as gaseous or dissolved ammonia as well as in organic form within the mixed liquor and settled solids. In fact, AD can be seen as making ammonia gas emission even more problematic as it converts as much as 25% of the organic nitrogen to an inorganic or ammonia form.

Currently AD designs do not include processes for recovering nitrogen and phosphorous and thus they contribute little to the solution of key air and water quality problems. As a result of this limitation and the capital costs involved, many farmers are not willing to adopt AD technology which is likely why CAFO AD adoption, although growing, is not growing at a rate that would be expected or desired. This is in spite of the fact that CAFOs are under increasing scrutiny in regard to air emissions and odor (EPA, 2005), contributors to which include particulate matter, hydrogen sulfide, methane, nitrogen oxide, volatile organics, and ammonia. Development of an EPA policy for monitoring and evaluating CAFO ammonia emission is currently underway, and it is probable that this effort will result in new requirements (EPA, 2005).

Incorporating ammonia recovery into an AD process would be beneficial for two key reasons. First, the cost of commercial fertilizers is continually increasing, and technologies that recover nitrogen for use as fertilizer would be advantageous. Second, the incorporation would enhance odor abatement and decrease ammonia release to the air. Unfortunately, currently available ammonia removal and recovery technologies cannot be widely applied to animal waste due to the high level of solids in manure wastewater, and the extremely high cost of the technology.

Some biological processes such as nitrification/denitrification are commonly used in wastewater treatment. However, these processes do not produce usable fertilizer. Researchers (Tilche et al., 2001, Choi et al., 2005) have studied full-scale nitrogen removal from piggery manure wastewater with Sequencing Batch Reactor (SBR) nitrification and denitrification without AD. Vanotti (2004) studied full-scale swine wastewater ammonia removal with another nitrification and denitrification system, Anoxic/Oxic (A/O). These processes are technically effective, as Szögi (2006) reported that the annual ammonia emissions were reduced 90% in the swine wastewater lagoon treated by using nitrification and denitrification. However, these aerobic processes require a large reactor and large amount of electricity for the ammonia oxidation step as well as for oxidizing the organic material to $CO_2$. When treating AD effluent, a recently developed process, "anammox" (Fux and Siegrist, 2004) needed only 40–50% oxygen compared with traditional nitrification and denitrification, and organic material was not required. However, there have been few successful demonstrations of either municipal or industrial wastewater treatment using this technology.

Several physio-chemical processes, including ion exchange and ammonia stripping, allow removal and recovery of ammonia. Ion exchange can be precluded as a viable option for animal waste treatment because it requires extremely low solids concentrations. However, ammonia scrubbing shows potential due to its ability to meet the animal manure needs regarding solids concentration and cost. Three common methods are 1) using a biofilter to oxidize ammonia to nitrate; 2) burning the gas to oxidize ammonia to nitrogen gas; and 3) water absorption for strong ammoniac industry wastewater. Unfortunately, all stripping processes developed to date are not optimized for animal manure. While other technologies exist for ammonia removal and nitrogen recovery, they are generally too expensive to be adopted by farmers.

In addition to nitrogen or ammonia recovery there is a need for associated technologies to remove or recover phosphorous (P) from the AD effluent as P has been identified as a major contributor to waterway water quality degradation through eutrophication (Stickney, 1994). To mitigate the effects of discharged P, environmental regulations have been established in many regions (Rosenthal, 1994; Bergheim and Brinker, 2003; MacMillan et al., 2003). For example, in Idaho, which is now becoming a large CAFO producer, P discharge is being actively debated as a potential regulation parameter for the incoming CAFOs and regulation is expected to occur very soon. Generally, P removal technologies for wastewater include chemical and biological processes. Biological methods are not suitable for animal manure due to the extremely high P content within the manures. Chemical methods include settling, flocculation, precipitation and electro-coagulation with one particular technology, struvite crystallization, receiving considerable recent attention. The formation of struvite (magnesium ammonium phosphate or $MgNH_4PO_4.6H_2O$) requires the presence of three ions in solution, $Mg^{2+}$, $NH_4^+$ and $PO_4^{3-}$ which react to form precipitates with low solubility (pKsp of 12.6) (Wrigley et al., 1992; 2002; Jeong and Hwang, 2005). One of the advantages of this process is that the struvite product can be utilized and marketed as a slow-release fertilizer and value-added product. A struvite crystallizer designed as a cone-shaped fluidized bed reactor was used to achieve high P removal (80%) from swine wastewater (Bowers and Westerman, 2005) and high P removal as struvite precipitation was also expected from digested dairy effluent. However, surprisingly poor P removal (<15%) was obtained under various conditions using this crystallizer (Zhang et al., 2006) for treating the effluent from an anaerobic digester, although better performance (50%) was observed treating dairy lagoon effluent. The results indicated that although organic P was converted to an inorganic form after anaerobic digestion, it was not available in an ionic form as is commonly believed. Instead, the majority of the P was in a suspended solid form, contained in particles smaller than 74 μm, with half or more in particles 2.5 μm or smaller. The high calcium content (about 1,000 mg/L) in the effluent may have contributed to the presence of P as a particulate by forming a calcium-phosphate suspended solid in the dairy effluent. Struvite crystallization requires dissolved reactive phosphate to form and the calcium-phosphate solids, with low solubility, provided little reactive phosphate, thereby blocking struvite crystallization, thus resulting in poor P reduction.

Unfortunately, physical solid-liquid separation processes for the removal of P associated with solids (e.g. sedimentation, screening, and filtration) generally have low efficiency because the majority of the solids are in fine particulate form in the manure wastewater (Zhang et al., 2006). Brownian motion and fine particle mass produce very slow sedimentation of the colloid particles in the water. Use of coagulants and flocculants can enhance the solids and P removal by aggregating fine particles to facilitate rapid settling and screening. Coagulants and/or flocculants destabilize and combine the suspended charged particles, resulting in larger particles or floc formation that separate more easily from the water. However, polymer usage would significantly increase process costs. For instance, the cost of the necessary chemicals is about $2.63 per 1,000 liter wastewater (Oh et al., 2005).

The prior art has thus-far failed to provide a system for the treatment of animal waste that recovers both nitrogen and phosphorous in a useful, commercially viable form, and that is economical enough to be employed by the farming community.

SUMMARY OF THE INVENTION

The present invention provides a flexible, integrated system and method for the recovery of nutrients residing in the effluent from the anaerobic digestion of animal waste. The resulting final effluent that is produced can be safely stored without releasing noxious odors and phosphorous contamination and later can be more effectively applied to limited CAFO land as a fertilizer without fear of chemical burning. The system and method also generates valuable products such as fertilizers and scrubbed biogas. Importantly, the method is "integrated" in that raw biogas produced in an early step of the method is used to treat ammonia-scrubbed effluent in order to lower its pH to acceptable levels. In so doing, impurities in the biogas are absorbed by the effluent, thereby cleaning the biogas.

Briefly, the method involves the steps of anaerobic digestion (AD) of the animal waste to form biogas and AD effluent; mechanically separating fibrous solids from the AD effluent; settling solids from the effluent and removing this P-enriched solid; increasing the pH of the effluent; stripping ammonia from the effluent; and lowering the pH of the ammonia-stripped effluent by exposure to the raw biogas that was produced by AD, a step which concomitantly scrubs the biogas. Resulting products are a more valued scrubbed biogas and two nutrient products, a P-rich solids containing nitrogen and potassium as well as organic fibers as well as a ammonia salt slurry

BRIEF DESCRIPTION OF THE DRAWINGS

FIGS. 2A and B. Schematic representation of A, two-tower closed loop ammonia stripping and acid absorption system; and B, one tower closed loop ammonia stripping and acid absorption system.

FIG. 3. Schematic illustration of an anti-clogging tray with gas guiding holes. A, top view; B, side sectional view.

DETAILED DESCRIPTION

The method and system involves the anaerobic digestion (AD) of the waste, removal and recovery of phosphate containing solids from the waste, and stripping and recovery of ammonia from the waste. In one embodiment, the method and system is "integrated", meaning that a product of an early step of the method (raw biogas production via AD) is used to carry out a later step of the method (decreasing the pH of high-pH ammonia-stripped effluent). When high-pH effluent is exposed to raw, untreated biogas, impurities in the biogas (e.g. $CO_2$ and $H_2S$) are absorbed by the effluent. Absorption of $CO_2$ and $H_2S$ lowers the pH of the effluent even as it removes these "contaminants" from the biogas, thereby cleaning the biogas. This step may alternatively be described as using a product of one of the last steps of the method (high-pH ammonia-stripped effluent) to purify a product of an early step of the method (biogas), and in the process lowering the pH of the effluent. This dual purpose step serves to integrate the method by advantageously connecting early and late method steps to form desirable products (scrubbed biogas and low pH ammonia-scrubbed effluent). The biogas so produced is more "engine-friendly" than raw, unscrubbed biogas and can be more effectively and economically used in an electrical generator set or as a potential compressed fuel. The low-pH ammonia-stripped effluent (from which phosphorous had already been removed) can be stored safely, e.g. in an agricultural lagoon, without emitting noxious odors or contaminating the land and water with phosphorous or high pH material. A flow chart that schematically depicts this process is presented in FIG. 1.

Brief Outline of the Method

Figure 1:
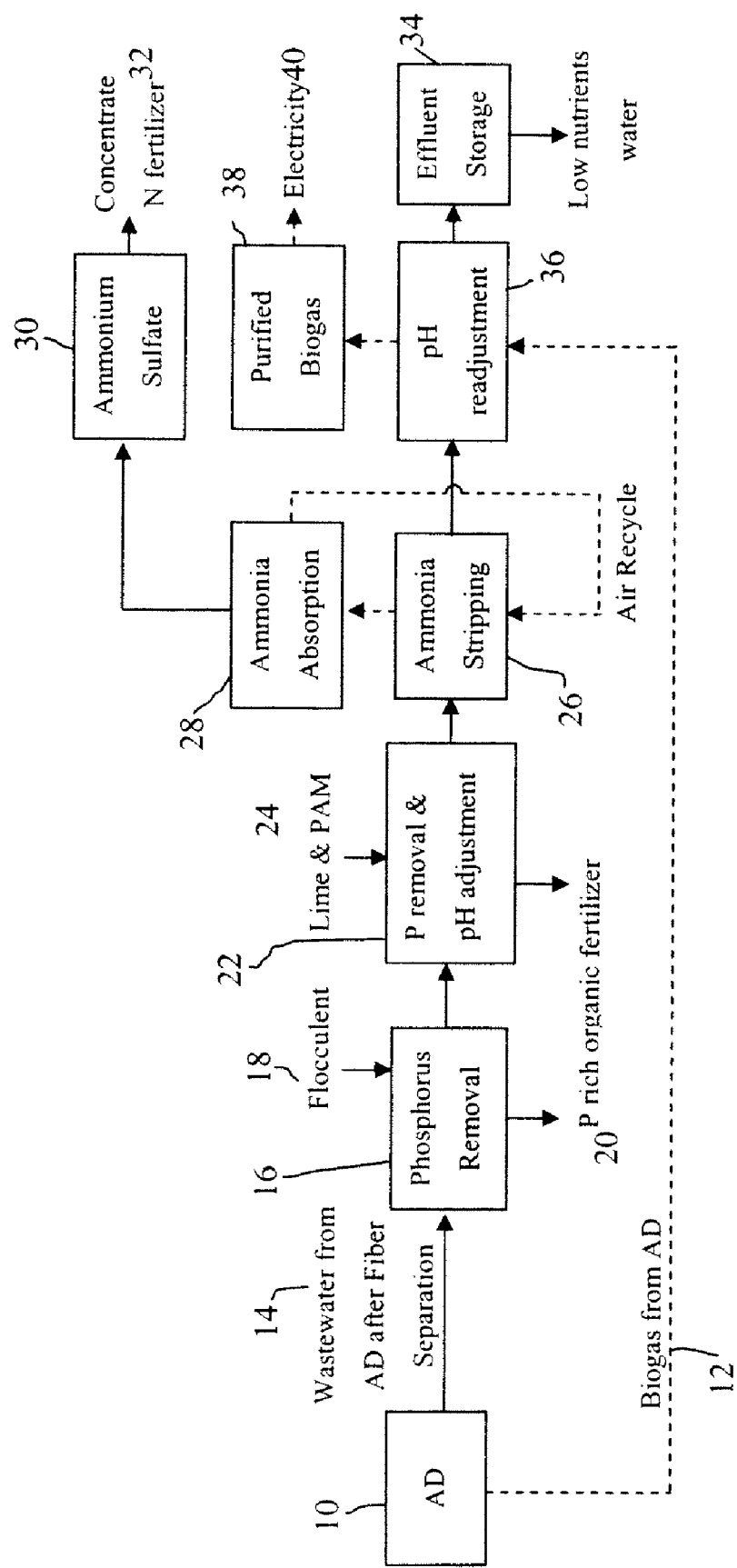
FIG. 1. Flow chart that schematically depicts the animal waste treatment process.

The first step of an exemplary method is anaerobic digestion (AD) of the animal waste to form raw biogas and AD effluent. FIG. 1 shows an AD system 10 in which animal waste is subjected to anaerobic digestion to produce raw biogas 12 and wastewater 14 after fiber separation has occurred. A variety of AD reactor designs can be employed including but not limited to complete mix, plug flow, axial mixed plug flow, upflow, sludge blanket, sequencing batch, fixed film, hybrid, and temperature phased. Raw biogas 12 typically contains contaminants such as $CO_2$, and $H_2S$. Wastewater 14 from an AD system 10 typically contains excess phosphorous, nitrogen, as well as solids and particulate material and other byproducts.

Phosphorous removal can be achieved in a two step fashion. Wastewater 14 proceeds to a first phosphorous removal stage 16 where settling of the solids occurs. In some embodiments, this first settling step may be enhanced, e.g. by the addition of settling agents or "flocculants" 18, such as biopolymers. The settled solids are separated from the supernatant (e.g., the supernatant may be pumped off or the solid sludge may be pumped away) and the solids may be used as fertilizer (e.g., P rich organic fertilizer 20). This P rich fertilizer is advantageous not just because of its high concentration of desired P, but in that it also contains within its solid matrix other important nutrients including organic nitrogen, potassium and fibrous organic carbon. The pH of the separated supernatant is then raised in a second stage 22 by the addition of a suitable agent 24 in preparation for ammonia stripping. The suitable agent may be, for example, lime, which is relatively inexpensive in bulk form; however, other suitable agents known in the art may also be employed. Typically, the AD effluent has a temperature of about 35° C., and in this case, the pH should be raised to about 10. However, if the AD effluent temperature is for any reason lowered during the solid removal process, the optimal pH will increase. Generally, a pH range of about 9.5 to about 12 will suffice, with pH 11 being sufficient for a temperature of about 20° C., and pH 10 being sufficient for a temperature of about 35° C. The addition of lime 24 also initiates a second solids settling step because, in addition to increasing the pH, lime promotes precipitation of calcium phosphate, calcium carbonate and other organic materials. These solids can also be collected and used as fertilizer 20, either in and of themselves, or in combination with solids recovered in the first solids settling step.

The high-pH supernatant is then sent to a closed-loop ammonia stripping system 26 that is optimized to handle the relatively high levels of solids and ammonia found in animal waste. Optimization is carried out by adjusting parameters such as the temperature and pH of operation, tower height, composition and design of packing materials and trays, etc. Ammonia stripped by the ammonia stripping system 26 is then absorbed in an ammonia absorption stage 28 by the addition of sulfuric acid to make concentrated liquid ammonium sulfate 30, which can be removed and used as a concentrated nitrogen rich fertilizer 32. Other acids known to the practitioners of the art, such as phosphoric acid, could be utilized in lieu of sulfuric acid. Of importance is the use of the acid as a chemical binder to the stripped ammonia, thus releasing it from the air for its later reuse in the closed loop system. The resulting solution or slurry is composed of ammonia salts such as ammonia sulfate or ammonia phosphate, depending upon the particular acid agent that is used.

The ammonia-stripped effluent is eventually to be stored, e.g. in an agricultural lagoon 34. However, immediately after stripping, the effluent still has an unacceptably high pH. To lower the pH to levels acceptable for open-air storage, raw biogas 12 generated in the first AD step is bubbled through the effluent in a pH readjustment stage 36, thereby reducing the effluent pH (e.g. to about 8) due to the absorption by the effluent of $CO_2$ and $H_2S$ from the raw biogas 12. Importantly, this step also has an advantage in that the movement of $CO_2$ and $H_2S$ from the biogas 12 into the effluent serves, at the same time, to purify the biogas by reducing its $CO_2$ and $H_2S$ content. The purified biogas 38 is thus scrubbed and rendered more suitable for use, e.g. in engines, as a compressed fuel, and in the generation of electricity 40 etc. In other words, the pH of the ammonia-stripped effluent is reduced and the biogas is scrubbed in a single step of the integrated method.

The following discussion describes each step of the method in detail.

Anaerobic Digestion

The first step of the method is anaerobic digestion of animal waste. By "animal waste" we mean both solid and liquid waste from animals (e.g. manure, urine, etc.). Such waste may be from any type of animal, and will usually be from animals that are raised in large groups (e.g. for commercial purposes) where large amounts of waste are generated and disposal is a problem. Examples of such animals include but are not limited to cattle, pigs, horses, sheep, goats, chickens, turkeys, geese, etc. In addition, many processes now involve a co-digestion approach where a mixture of animal manure and organic fraction municipal solids such as food scraps and food processing waste are co-mingled and digested. The technology is particularly suited to handle waste from large agricultural operations that raise significant numbers of animals, e.g. CAFOs. However, use of the method need not be confined to agricultural endeavors or to the treatment of animal waste. For example, the methods may also be adapted and utilized by zoos, animal parks, or other organizations that care for multiple animals, or by municipalities to process human waste, etc. Further, other types of waste products such as the aforementioned organic fraction of municipal solids or combinations thereof with manures, may also be processed by the method. The efficient integrated methods and systems of the invention may be adapted and used in any situation where there is a need treat organic waste.

Those of skill in the art are familiar with anaerobic digestion and various methods and apparatuses for carrying out anaerobic digestion of waste. Briefly, anaerobic digestion is a process in which microorganisms break down biodegradable material in the absence of oxygen. Initially, bacteria hydrolyze the insoluble organic polymers (e.g. carbohydrates) in the waste material, thereby making them available for other bacteria. Acidogenic bacteria then convert the hydrolysis products (e.g. sugars and amino acids) into carbon dioxide, hydrogen, ammonia, and organic acids. Acetogenic bacteria then convert the organic acids into acetic acid, along with additional ammonia, hydrogen, and carbon dioxide. Finally, methanogenic bacteria convert these products to methane, which can be recovered as biogas, and carbon dioxide. Anaerobic digestion may be carried out, for example, using a variety of designs and methodologies as described in Metcalf and Eddy (2003). The gaseous methane (biogas) produced by AD is impure due to the presence of contaminants such as $CO_2$, and $H_2S$. In the practice of the present invention, the raw biogas is retained and is utilized in a later step of the method, as described in detail below. The first-stage liquid AD effluent contains solids and particulate matter with large amounts of ammonia and phosphorous, which must be removed.

First Settling and Separating of Phosphate-rich Solids

Phosphate-rich solids may be removed from the AD effluent using any of a variety of known settling techniques. Depending on the type and condition of waste that is being treated, it may be advantageous to also carry out an initial mechanical separation (e.g. belt press, slope screen, etc.) step to remove large solids and particulate matter prior to solid settling.

Settling of solids may be carried out by any of several biological or chemical methods that are known to those of skill in the art. In one embodiment of the invention, a chemical procedure is used, examples of which include but are not limited to settling, flocculation, precipitation, electrocoagulation, struvite crystallization, etc. A preferred method is settling in combination with flocculation.

Flocculation involves the removal of phosphate and other suspended solids through physical solid-liquid separation processes, such as sedimentation, screening, and filtration. These processes, without adding coagulant and/or flocculent polymers, generally have a low efficiency because the majority of the solids are in fine particulate form in manure wastewater. Brownian motion and fine particle mass produce very slow sedimentation of the colloid particles. Coagulants and flocculants can be used to enhance solid and phosphate removal by aggregating fine particles to facilitate rapid settling and screening. Common coagulants that may be used in the practice of the present invention include but are not limited to inorganic compounds, such as aluminum sulfate (alum), ferric sulfate, and lime (CaO). Polyacrylamides (PAMs), which are high molecular weight long chain water-soluble polymers, may also be utilized. The addition of coagulants and/or flocculants destabilizes the suspended charged particles and builds "bridges" between suspended particles, resulting in larger particle or floc formation that separates more easily from liquid effluent. In addition, most of the fine suspended particles in wastewater are negatively charged. The negative surface charge keeps the particles dispersed in wastewater due to electrostatic propulsion, resulting in stability of the particle suspension. The stability must be broken down before the particles can be aggregated, for example by the addition of polymeric cationic flocculants. Cationic polymers have numerous amine groups with strong positive charges, which neutralize the negative charges on the particle surface, and they may thus be used to neutralize the surface charges of fine particles in wastewater. Furthermore polymers may act as "bridges" between suspended particles and bridged particles interact with other particles resulting in an increase in floc size, thus enhancing settling of the particles.

Several types of cationic flocculants are suitable for use in manure effluent. These include but are not limited to polyethylenimines (PEIs), which comprise branched polymers with different molecular weights and positive charges, and strong cationic polymers such as the commercially available KlarAid PC.

In a preferred embodiment of the invention, much of the solids are removed through settling, with the remaining P-rich solids being removed by flocculation using strong cationic polyamine polymers. Two polyamine polymers may be added to the effluent. The first is a cationic polymer of low molecular weight (MW) in the range of from about 3,000 to about 15,000. The chief goal of adding such a low MW polymer is to destabilize the negative particles by charge neutralization. The dosage of this polymer depends on particle content and charge density. Preferably, the particles still retain a weak negative charge after the addition of the low MW polymer. The second polymer is then added and is adsorbed onto the particle surfaces, thereby forming a large floc that will settle out of the effluent, or can be otherwise removed. The preferred MW of the second cationic polymer will be in the range of from about 0.7 million to about 2.0 million.

After solids have settled sufficiently from the AD effluent, they are separated from the supernatant. This can be accomplished by any suitable means, e.g. by pumping the supernatant into a receiving tank and leaving the solids behind, or vice versa by pumping out the settled solids. The solids, which are in the form of a sludge, are rich in phosphorous, and may be recovered and used as fertilizer or in the preparation of fertilizer, with or without further treatment, e.g. drying, dewatering, etc. Dewatering of the solid precipitate (sludge) may be necessary in order to reduce the sludge volume and increase the liquid volume for ammonium nitrogen recovery. Any suitable means for carrying out this step may be employed, e.g. a screw or other type of press may be used for dewatering. As described above for other solids, dewatered sludge can be exported off the farm or sold as phosphorous rich fertilizer. Alternatively, it may be reused on the farm of origin and/or mixed with the sludge obtained in a later step of lime dosing.

Increasing the pH of the AD Effluent

The AD effluent (i.e. the supernatant from the previous step) is then prepared for the step of ammonia stripping by increasing the pH. This is typically accomplished by the addition of an agent such as lime. The pH is generally increased to a value in the range of about pH 9 to about pH 11, and preferably to about pH 10. Lower pH values which still allow for effective free ammonia accumulation are preferred, because subsequent treatment of the effluent after ammonia stripping (see below) requires lowering of the pH to preferably at least eight before final storage of the effluent.

The addition of lime to increase the pH has another beneficial effect: it causes the precipitation of additional phosphorous-containing solids from the effluent, e.g. primarily calcium carbonate, but also calcium phosphate, and intermixed fibrous organic material. Therefore, a second settling and separation step is generally included at this point in the process.

Second Settling and Separating of Phosphate-rich Solids

The solids that are precipitated when the pH of the effluent is increased are also settled and removed. This step is generally carried out by using the processes described in the earlier P-solids removal step.

As with the first settling step, the solids that are produced are rich in phosphorous and may be recovered with or without further treatment for use as fertilizer. In a preferred embodiment of the invention, all phosphorous-rich solids produced according to the method (i.e. those from both the first and second solid settling/precipitation steps) are combined to form a single product that can be used and/or sold as fertilizer due not only to the presence of high concentrations of P but also because they contain other important nutrients such as the aforementioned salts, organic nitrogen and fibrous organic carbon. Notably, the solids are also significantly pathogen free because of the earlier integrated step of anaerobic digestion, thus allowing for a better market price, especially in use with organic farms.

Stripping Ammonia from the High-pH Effluent

The high-pH effluent is next subjected to ammonia stripping. Ammonia stripping is a simple desorption process that is used within wastewater treatment industries, and research has confirmed that it is a valuable and reliable ammonia removal technology (Liao et al., 1995; Siegrist, 1996; Cheung et al., 1997; Katehis et al., 1998; Bonmatí et al., 2003; Siegrist et al., 2005; Zeng et al., 2005;). Briefly, stripping is a distillation procedure that consists of separating fluid components by differences in boiling point or vapor pressure. The usual means of separation is through a column or tower that is packed with one or more various support materials, i.e. Pall Rings, Raschig Rings, Berl Saddles, etc., to increase contact surface. A stripping medium (e.g. hot air or steam, or, in one embodiment of this invention, unheated air) is injected into the bottom of the tower and an ammonia containing solution is injected at or near the top. As the ammonia containing liquid trickles down through the packing, it contacts the rising hot vapor and the more volatile ammonia fraction is vaporized and can be collected and further treated. The less volatile liquid component becomes increasingly purer as it nears the bottom of the tower, where it may be collected.

In some embodiments of the present invention, ammonia stripping is carried out using a closed loop tower design that uses air as the stripping medium and includes an acid absorption system to capture ammonia as ammonium salt. Air is a preferred embodiment for this process because, although it does not have as high an ammonia absorbance capacity as other potential carrier gases, air is inexpensive and the pH adjustment needed can be maintained at a relatively low level (e.g. pH 10) because the process takes advantage of the hot (~32-35° C.) manure wastewater coming from the anaerobic digester to compensate.

The system that is used for ammonia stripping may be of any suitable design. For example, a two-tower system as illustrated in FIG. 2A may be used. In the two tower system, a first tower 42 is used for ammonia stripping. The waste water effluent 44 is injected near the top of the first tower 42. Air 46 is directed into the bottom of the first tower using a fan or blower 48. The air accumulates volatilized ammonia and, with the pressures developed by the fan or blower, is sent to the bottom of the second tower 50. This ammonia enriched air is blown upward as acid is sent from the top of the second tower 50 down through the media, absorbing the ammonia from the air. The resulting air, now ammonia free is returned back to the bottom of the first tower for continuation of the process. The acid injected into the second tower 50 is sulfuric acid or a similar acid with the capability to combine with ammonia to form an ammonia salt Alternatively, a single tower design may be used, as illustrated in FIG. 2B. A single tower 52 includes wastewater input 54 for ammonia stripping and acid input 56 for acid absorption. Air 58 is directed into the bottom of the tower 52 using the fan or blower 60. As can be seen in both the single and two-tower systems, according to the design, air circulates in an enclosed system, thus allowing for enhanced ammonia recovery and a reduction in energy inputs as the air without outside influence maintains its temperature for a longer period of time. In some embodiments of the invention, the air is heated, e.g. to a temperature of about 50° C., or in the range of from about 40° C. to about 60° C. In one embodiment, heat is supplied by excess generator heat from the AD process. However, in a preferred embodiment of the invention, the air is not directly heated, but instead is indirectly heated through the continual input of 30-35° C. manure wastewater coming from the AD process, and is re-circulated and re-used continually. The air enters the bottom of the stripping section and flows upward, absorbing gaseous ammonia while moving toward the top of the ammonia stripping section of the tower. The action of the flow coupled with the use of a blower or fan sends the ammonia saturated air into an acid section of the tower. In a preferred embodiment, the acid section contains sulfuric acid and, as the ammonia saturated air flows through the acid, the ammonia reacts with the acid to form an ammonium sulfate solution, which is removed. The resulting ammonia depleted air is then circulated back to the stripping section to accumulate additional ammonia, and so on. The result is a continuous, closed system whereby the same air can continually be used to absorb and release ammonia over and over again, resulting in significant cost savings in regard to electricity and heating.

Conventional ammonia stripping systems are not designed to deal with the usual amount of solid matter in AD effluent. Whereas the acid absorption tower (two-tower system) or the acid absorption portion of the tower in a single tower system may employ conventional small packing material in order to take advantage of its high efficiency, the AD effluent may tend to clog small packing material in the ammonia stripping section. The stripping towers of the present invention may therefore be specially designed to solve this problem, and the tower design may be tailored to accommodate the particular type of animal waste that is being treated. In one embodiment, a traditional tower is used but it is packed with coarse packing material and a relatively short packing height is used. For example, a tower with an inner diameter of 4" with a 1" pall ring and a packing height of 5' may be utilized with a feed flow of up to at least about 10 g/L of TS. In general, plastic packing material with a nominal diameter no less than 2" and a specific area of 80-120 $m^2/m^3$ is preferred. Although smaller packing material or packing material with higher specific surface area will be better for mass transfer, it will be more easily clogged. A lower packing height (3-5 m) compared with the conventional 6.1-7.6 m is also preferred in order to reduce clogging.

Alternatively, a novel tray tower with specially designed anti-clogging trays may be employed. Such anti-clogging trays are illustrated in FIGS. 3A and 3B. As can be seen, the tray 110 is substantially flat and contains one or more gas guiding holes 120, and, optionally, one or more additional holes 122 which permit the flow of air and liquid through various trays. The gas guiding holes 120 include a spaced apart cover which protects against the packing material in the tower from sealing off the gas guiding holes 120. Furthermore, the cover is opened in a direction desired for movement of gas and liquid (as described in more detail in conjunction with FIG. 4). The tray 110 may be of any suitable shape for example, substantially round, square etc. so long as the trays properly fit into and can be stably attached within the tray tower.

Figure 4:
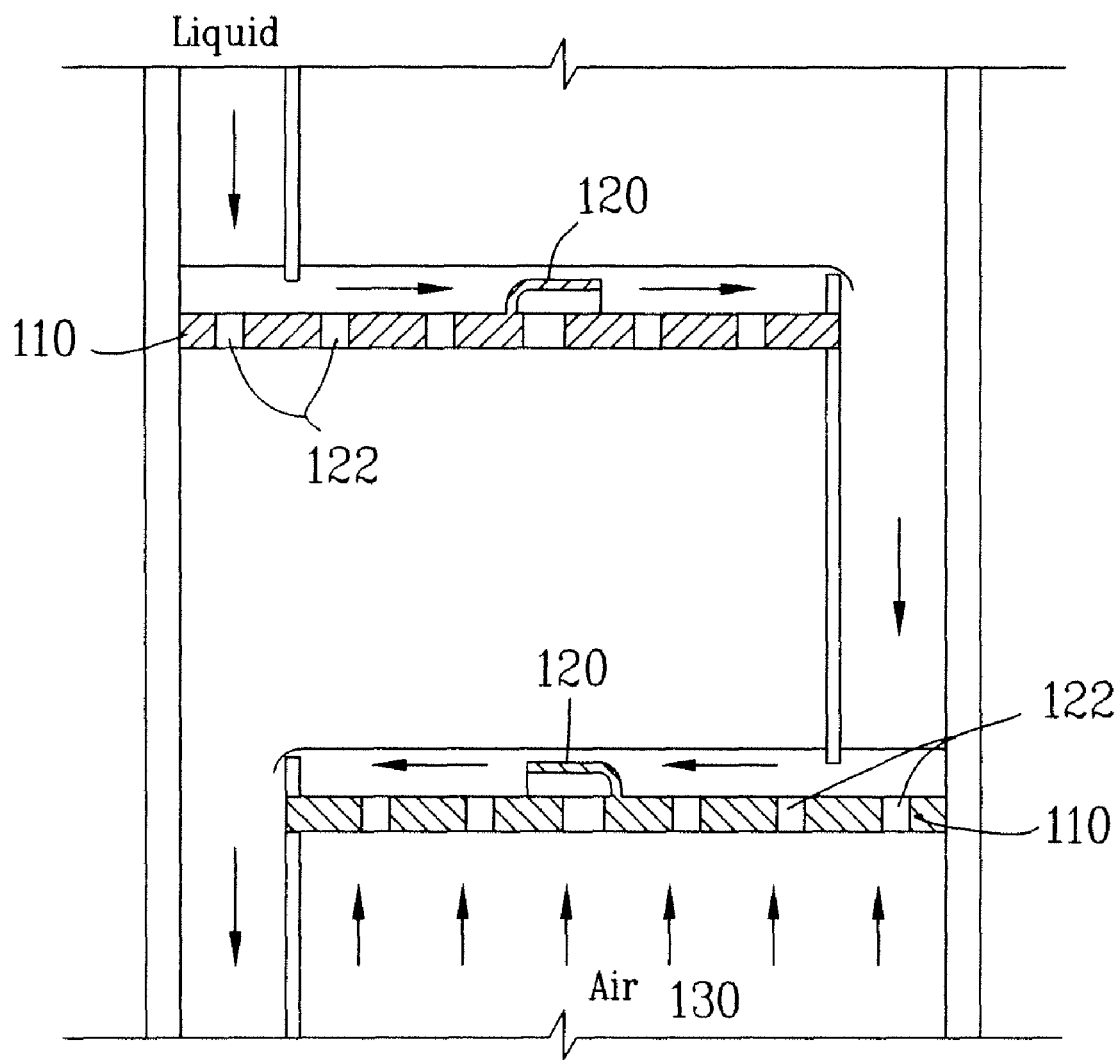
FIG. 4. Schematic illustration of a tray tower that utilizes the anti-clogging trays of the invention.

A schematic illustration of a tray tower employing such anti-clogging trays is depicted in FIG. 4. According to this embodiment of the invention, a gas such as air 130 is forced through gas guiding holes 120 and additional holes 122 in order to blow the liquid passing over the tray 110 in the desired direction (indicated by the right and left arrows) and thus clogging is prevented. This kind of tray tower has been shown in laboratory tests to lead to no clogging using even a substrate with an extremely thick "porridge-like" consistency.

Figure 8:
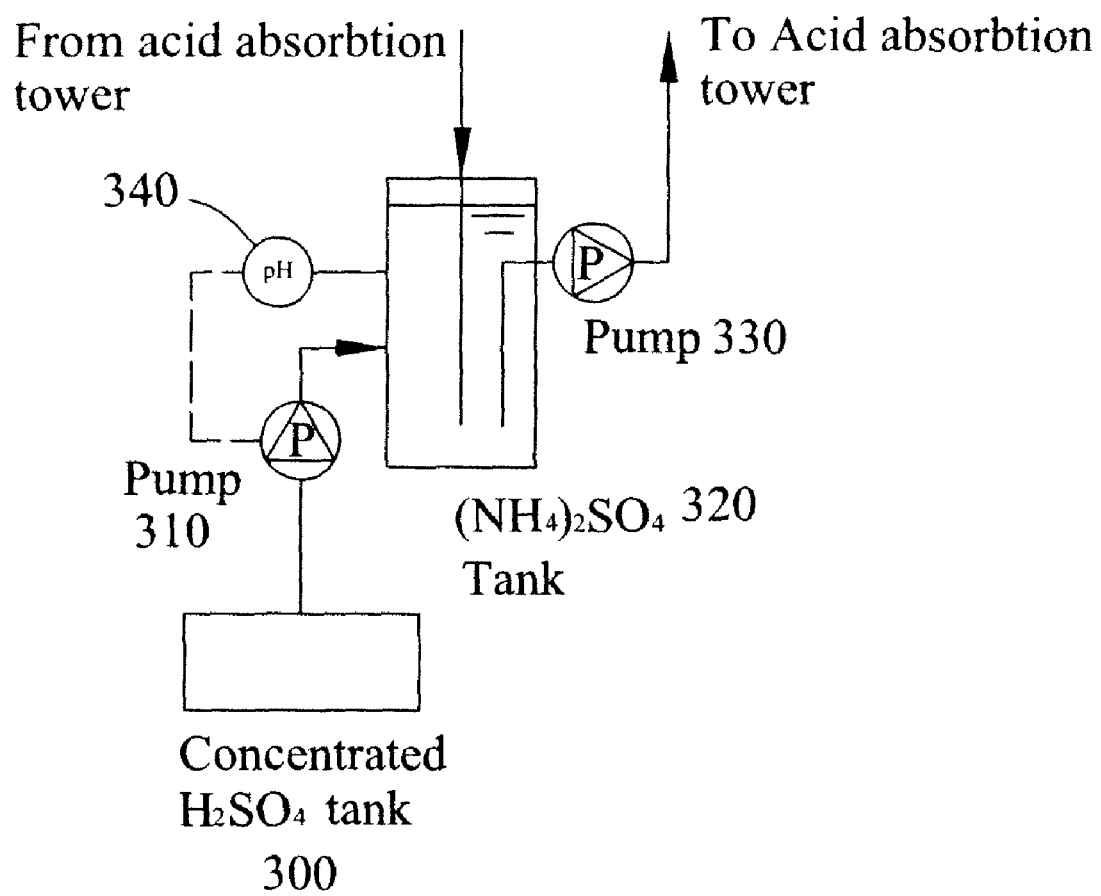
FIG. 8. Schematic illustration of acid dosing for the acid absorption tower.

The schematic illustration of acid dosing for the acid absorption tower is shown in FIG. 8. This system protects the acid absorption tower working at acid concentrations lower than 0.3N sulfuric acid but still can attain an ammonium sulfate concentration higher than 40% by weight. Concentrated sulfuric acid, 98% by weight, is stored in tank 300. Initially, ammonium sulfate tank 320 is filled to 40-60% capacity with water which absorbs ammonia from the stripping process. As long as the pH is higher than 3, concentrated acid is added to ammonium sulfate tank 320 with pump 310, which is controlled by online pH probe 340. The addition of concentrated acid is stopped when the pH is lower than about 0.5-1.0. The acid addition is suspended when the solution pH is below 3 because no ammonia is stripped out in the acid absorption tower at this pH because of the $NH_3$ and $NH_4^+$ balance in the solution.

The ammonium sulfate that is formed is removed and may be used as a fertilizer. The high-pH, low ammonia effluent is further processed as described in the following section.

Exposing the High-pH Effluent to Biogas Produced by AD: Biogas Scrubbing

The effluent that remains after ammonia stripping is low in both phosphate and ammonia. However, the pH of this effluent is relatively high and thus it is not suitable for open storage (e.g. in an agricultural lagoon) or for application to land unless the pH is decreased. According to the integrated method of the invention, this is accomplished by exposing the high-pH effluent to the impure biogas that is produced by the first anaerobic digestion step of the method. Exposure can be carried out in any known manner, and will generally be accomplished by sparging the biogas through the effluent. As the impure biogas is bubbled through the effluent, impurities such as $CO_2$ and $H_2S$ are removed from the biogas by absorption into the effluent. Removal of the impurities is beneficial since this purifies or scrubs the biogas, making it more suitable for use. Absorption of $CO_2$ and $H_2S$ by the effluent is beneficial because it lowers the pH of the effluent to acceptable levels e.g. to about pH 8. Bubbling biogas through the ammonia stripping effluent is beneficial for both the effluent and the biogas. Lab experiments showed that the pH of the stripping effluent can be lowered from pH 9.7 to pH 8.4. Simultaneously, biogas components $CH_4$, $CO_2$, and $H_2S$ changed from 65.4%, 34.5%, and 0.14%, respectively, to 85.0%, 15.0%, and undetectable, respectively, when a biogas/liquid ratio of 9.6 v/v was employed.

The biogas scrubbing process can be carried out using a variety of techniques. For example, either shallow, coarse bubble or fine bubble aeration may be used. Shallow coarse bubble aeration is typically utilized when the biogas/liquid ratio (v/v) is large, e.g. higher than 15 for a pH 10 liquid. In contrast to fine bubble aeration, coarse bubble aeration requires only a small drop in pressure so it does not require the use of a blower. For fine bubble aeration, a blower is included to provide the requisite pressure. While this adds somewhat to the complexity and cost of the system, fine bubble aeration can be operated with deeper liquids than can coarse bubble aeration and results in higher impurity removal efficiency. Fine bubble aeration can be used when the biogas/liquid ratio (v/v) is low, e.g. < than 15 for a pH 10 liquid. However, since the liquid cannot absorb more $CO_2$ or $H_2S$ after it is saturated, in most cases, using fine bubble aeration with high biogas/liquid ratio (v/v) is not necessary and will not remove any more biogas impurities than does shallow coarse bubble aeration. In a preferred embodiment, the integrated process uses the less expensive and less complex shallow coarse bubble technology.

In general, this scrubbing procedure lowers the pH of the low-phosphate, low-ammonia effluent to a value in the range of from about 7 to about 9, and preferably to at least about 8. At these pH values, the effluent is safe for open-air disposal or storage.

Integrated System

The invention also provides an integrated system for the treatment of animal waste. The system comprises: a settling and flocculation reactor (mainly for phosphorus removal), a pH adjustment reactor, an ammonia stripping and absorption component (which can be combined in a single tower or may be housed in two separate towers), and a biogas purification reactor.

Flexibility of the Method

The method steps of the invention are described in detail above and are presented in an order that coincides with one embodiment of the invention. However, one advantage of the invention is that it is inherently flexible with respect to the order in which the various steps are carried out, and may be adapted or tailored to meet individual needs or capabilities of the user. The inherent flexibility arises at least in part from the use of at least one lime settling step to remove solids, and the use of trays and/or media that are capable of handling relatively high concentrations of solids, as compared to other known processes. The ability to handle high amounts of solids during ammonia stripping allows added flexibility regarding the ordering of the steps of the method. For example, in some embodiments, the removal of high phosphate solids is carried out after ammonia stripping. Alternatively, one or more steps of high P solid removal may be carried out prior to ammonia stripping and one or more additional steps of high P solid removal may be carried out after ammonia stripping. Various other permutations will occur to those of skill in the art, and all such variations are intended to be encompassed by the invention. Similarly, the elements of the integrated system may be set up in any of several variant configurations as required, in order to accommodate the method steps in whatever order, and/or with as many repetitions of one or more steps, as desired.

The invention is further illustrated in the following non-limiting examples.

EXAMPLES

Example 1

Exemplary Waste Treatment System

An exemplary waste treatment system is used to treat liquid animal waste (AD effluent after fiber separation) from 500 cows. A schematic representation of the system is presented in FIG. 5. The process carried out by the system includes flocculation for phosphorus removal, lime dosing for pH increase, ammonia stripping, acid absorption, biogas purification, and solid dewatering. The flow rate is 80 m³/d (21,000 gallons/d), reference to a commercial dairy farm.

Flocculation

Figure 5:
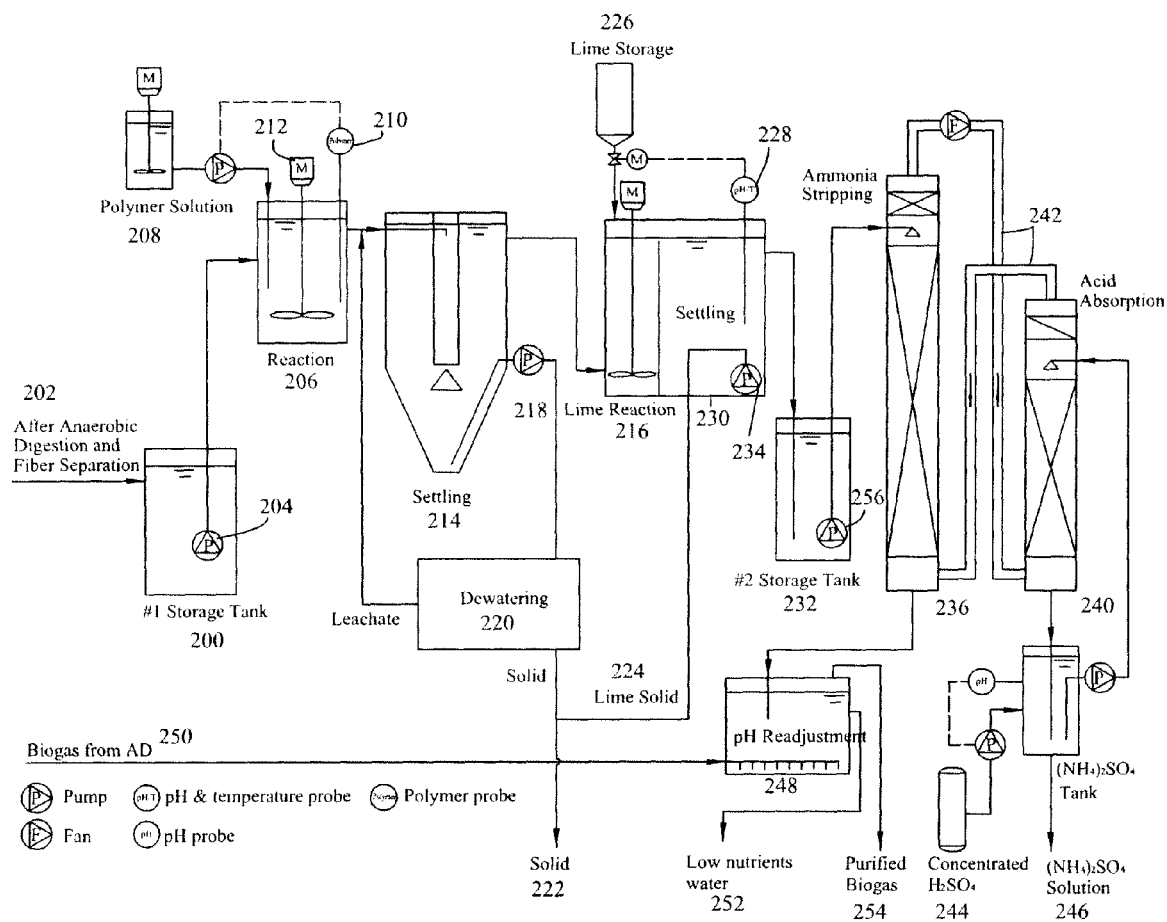
FIG. 5. Schematic representation of an integrated animal waste treatment system.
Figure 6:
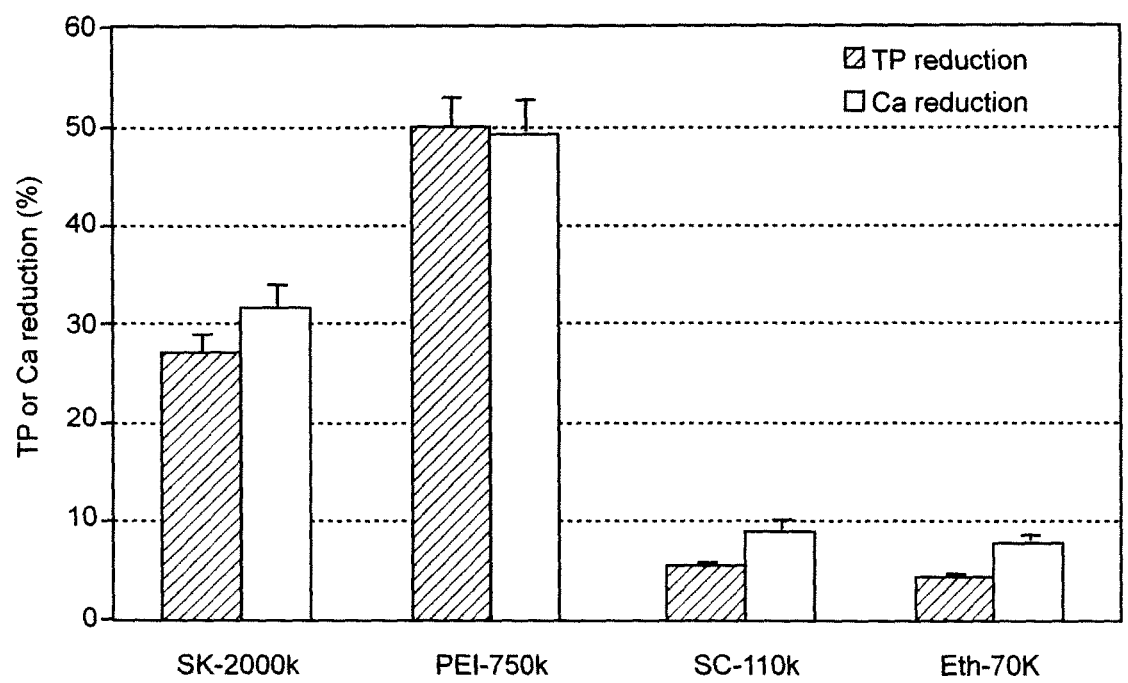
FIG. 6. Effect of PEI type on TP and calcium reduction.
Figure 7:
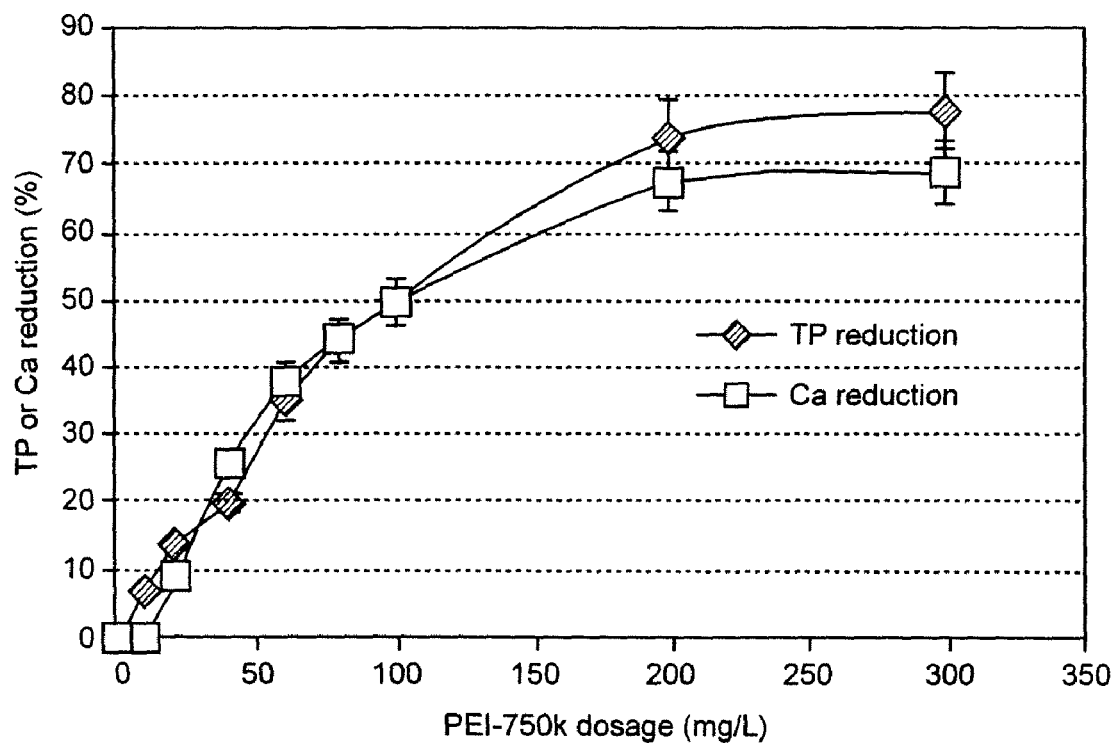
FIG. 7. Effect of PEI-750k dosage on TP and calcium reduction.

With reference to FIG. 5, the #1 storage tank 200 temporarily stores the AD effluent 202 and also acts as a flow equalizer. The hydraulic retention time (HRT) is two hours. The volume of this tank is 8 m³ (2,100 gallons), which includes 1.3 m³ (340 gallons) of headspace. An immersion pump 204 is installed to pump the liquid to the polymer reaction basin 206.

The polymer reaction time is 30 minutes. The reaction chamber 206 is 2.2 m³ (580 gallons), which includes 0.5 m³ (130 gallons) of headspace. A set of polymer dissolving/diluting systems 208 is employed for polymer dosing. Polymer dosing is controlled by an online polymer probe 210 located at the exit of the polymer reaction chamber 206. A motor driven stirring mechanism 212 can be used to accelerate and/or control operations in the reaction chamber 206. The mixture flows to the settling tank 214 by gravity.

The settling time in the polymer settling tank 214 is two hours, and the effluent thereafter flows to the pH adjustment system 216 by gravity. Settled sludge is pumped by pump 218 to the dewatering system 220. The settling volume is 6.7 m³, the headspace is 1.3 m³ (340 gallons), and the cone volume is 3.3 m³ (870 gallons). Dewatering is necessary in order to reduce the sludge volume and increase the liquid volume for ammonium nitrogen recovery. A screw press (not shown) is used for dewatering.

The dewatered sludge can be exported off the farm or sold as phosphorous rich fertilizer (solid 222). Alternatively, it is re-used on the farm and mixed with the lime sludge 224. The leachate recycles back to the settling tank 214 or to the #1 storage tank 200.

pH Adjustment

After flocculation, the flow of the liquid is reduced to 64 m³/d (17,000 gallons) because of solid discharge. Lime powder from storage device 226 is used for pH adjustment and further solid removal. Lime reaction time is one hour with lime powder directly added to the reactor 216. A pH probe 228 installed at the exit of the settling tank 230 controls the amount of lime added. The liquid mixture flows to the lime settling tank 230 by gravity. The lime reactor 216 is covered to prevent ammonium emission.

In the lime settling tank 230, the settling time is four hours. The settling tank 230 is covered to prevent ammonium emission. The liquid flows to the #2 storage tank 232 by gravity. Sludge is pumped out of the lime settling tank 230 using pump 234. The lime sludge is mixed with the dewatered polymer flocculation sludge and is exported off the farm.

The wastewater flow to the #2 storage tank 232 is 54 m³/d (14,000 gallons/d) because of lime solid discharge. The #2 storage tank 232 is covered to prevent ammonium emission. This storage tank 232 temporarily stores the AD effluent and acts as a flow equalizer as well. The HRT is two hours. A flexible bag is installed in order to keep the headspace pressure stable. The waste water is pumped by pump 234 to the ammonia stripping system 236.

Ammonia Stripping and Acid Absorption

The towers 236 and 240 for ammonia stripping (tower 236) and acid absorption (tower 240) have the same diameter (1 m). The stripping tower 236 has a packing height of 5.5 m and the absorption tower 240 has a packing height of 0.6 m. The air is circulated in a closed loop 242 to avoid ammonia emission and heating requirements.

The acid absorption system uses approximately 0.1N $H_2SO_4$ instead of concentrated $H_2SO_4$. The pH of the $(NH_4)_2SO_4$ will be kept below about 3.0 in order to obtain ammonia absorption and to avoid ammonia stripping. When the pH is above 3.0, concentrated $H_2SO_4$ from source 244 will be added to lower the pH to about 1.0. After the total $H_2SO_4$ added is more than 20% of the water by weight, the $(NH_4)_2SO_4$ concentration from tank 246 will reach 30%, and the solution is replaced with 0.1 $NH_2SO_4$ and the $(NH_4)_2SO_4$ is recovered.

pH Readjustment and Biogas Purification

The HRT of the pH readjustment chamber 248 is two hours. The depth of the wastewater is 0.5 m in order to utilize the biogas pressure in the AD. After exposure to the biogas 250, the water effluent will be at normal pH with low nutrients content 252. After the impurity absorption, the biogas 254 contains lower $H_2S$ and $CO_2$. Impurities can be further reduced if the biogas is passed through the lime settling solid.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. An integrated, closed loop system for treating one or more of animal waste and organic fraction municipal solids, comprising
   a biogas purification reactor for carrying out anaerobic digestion (AD) of said animal waste and organic fraction municipal solids,
   a biogas storage component,
   a flocculation reactor,
   a pH adjustment reactor,
   an ammonia removal component,
   an ammonia absorption component,
   an effluent storage component, said biogas storage component and said effluent storage component being connected so as to allow biogas stored in said biogas storage component to contact effluent stored in said effluent storage component.

2. The integrated, closed loop system of claim 1, wherein said ammonia removal component and said ammonia absorption component are housed in two separate towers.

3. The integrated, closed loop system of claim 1, wherein said ammonia removal component and said ammonia absorption component are housed in a single tower.

* * * * *